United States Patent

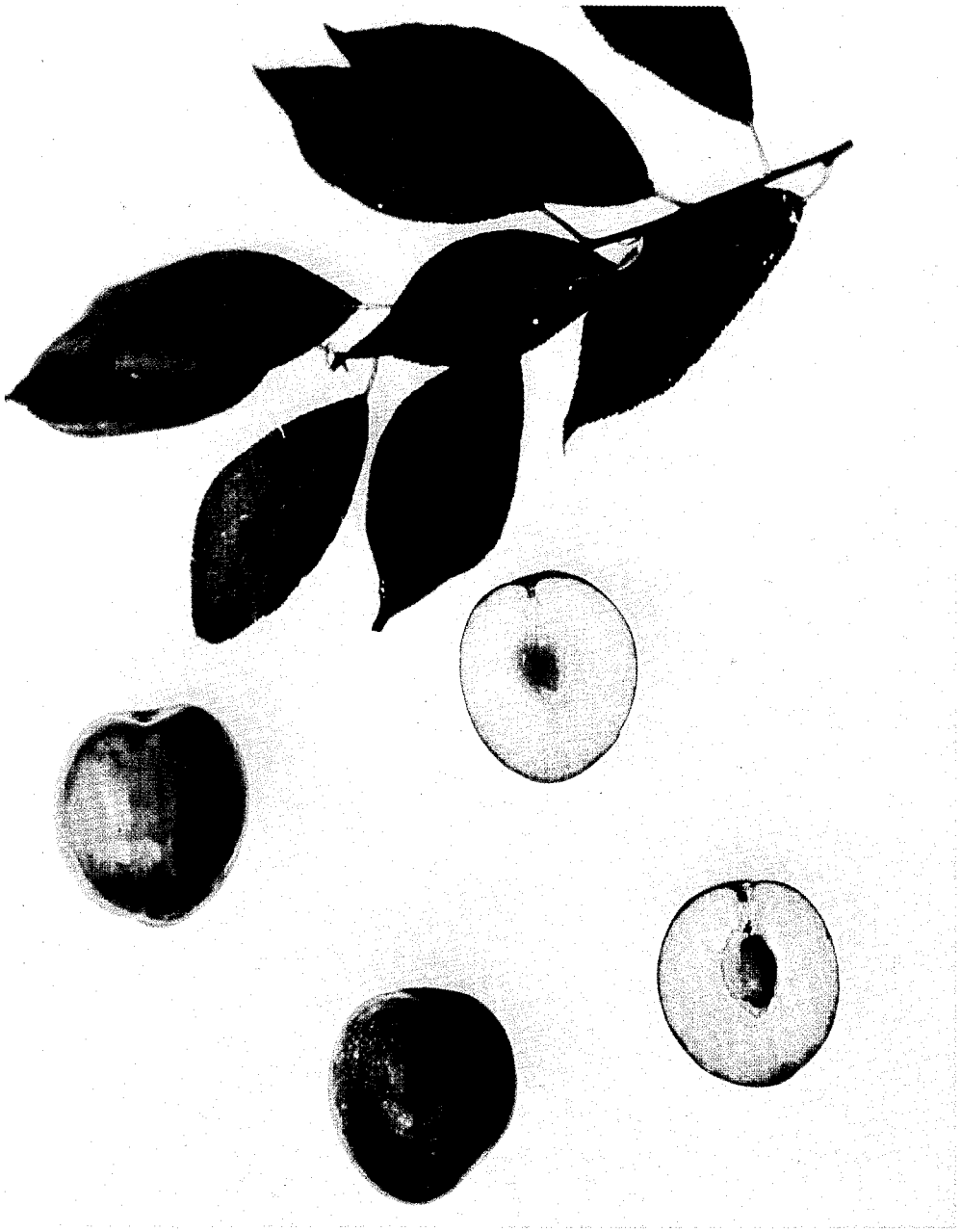

Plant Pat. 3,797

Patented Nov. 4, 1975

3,797

PLUM TREE

Frederic W. Anderson, Merced, Calif., assignor to The Burchell Nursery, Inc., Modesto, Calif.

Filed Dec. 23, 1974, Ser. No. 536,015

Int. Cl. A01h 5/03

U.S. Cl. Plt.—38 1 Claim

ABSTRACT OF THE DISCLOSURE

A plum tree which is large, vigorous, upright to spreading, open, foliated with medium size, ovate leaves having a crenate margin, blooming with medium size, white flowers, and a regular and very productive bearer of large to medium, uniform size, symmetrical, globose, semi-freestone fruit having yellow skin substantially entirely overspread with red, and yellow flesh.

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of plum tree resulted from my endeavors in the conduct of such plant breeding program.

ORIGIN OF THE VARIETY

A large number of open pollinated seedlings of the Eldorado (unpatented) plum were grown in my experimental orchard, located as aforesaid, under conditions of careful and continuing observation. In maturity, one of such seedlings evidenced characteristics which appeared desirable for commercial production. I, therefore, selected such one seedling—and which is the present variety—for asexual reproduction and with a view toward ultimate commercial introduction of such variety.

ASEXUAL REPRODUCTION OF THE VARIETY

Subsequent to its origination and selection as above, I asexually reproduced the variety in said experimental orchard by top-working on mature orchard trees, and such reproductions ran true, in all respects, to the original seedling tree.

SUMMARY OF THE VARIETY

The present variety of plum tree is large, vigorous, upright to spreading, open, foliated with medium size, ovate leaves having a crenate margin, blooming with medium size, white flowers, and a regular and very productive bearer of large to medium, uniform size, symmetrical, globose, semi-freestone fruit having yellow skin substantially entirely overspread with red, and yellow flesh; the tree, whose fruit is late ripening, being characterized—in comparison to the Casselman (unpatented), and which is the leading late-ripening plum in California—by heavier and more regular production of fruit, the latter having a brighter red color, fewer growth cracks and other fruit defects, and ripening a few days later. The tree is further characterized by blooming about with the Santa Rosa (unpatented).

BRIEF DESCRIPTION OF THE DRAWING

The drawing is an illustration, by photographic reproduction in color, of a twig with leaves, and separate fruit; one of the latter being cut in half to expose the flesh, and with the stone remaining in place in one of the cut halves.

DESCRIPTION OF THE VARIETY

The botanical details of this new and distinct variety of plum tree—with color definitions (except those in common color terms) referenced to Maerz and Paul Dictionary of Color—are as follows:

Tree:
- *Size.*—Large.
- *Vigor.*—Vigorous.
- *Growth.*—Upright to spreading.
- *Density.*—Open.
- *Production.*—Very productive.
- *Bearing.*—Regular bearer.

Trunk:
- *Size.*—Medium.
- *Texture.*—Medium.

Branches:
- *Size.*—Medium.
- *Texture.*—Medium.

Leaves:
- *Size.*—Medium. Average length—2¾". Average width—1⅛".
- *Form.*—Ovate.
- *Thickness.*—Medium.
- *Margin.*—Crenate.
- *Petiole.*—Medium length. Medium thickness.
- *Glands.*—Average number and position—2 to 5 on blade.
- *Color.*—Top side—Medium green (23–H–9). Under side—Lighter green (22–H–6).

Flower buds:
- *Length.*—Medium.

Flowers:
- *Blooming period.*—About with Santa Rosa. Medium, as compared with other varieties.
- *Size.*—Medium.
- *Color.*—White.

Fruit:
- *Maturity when described.*—Eating ripe—Sept. 15, 1974.
- *Date of first picking.*—Aug. 25, 1974.
- *Date of last picking.*—Sept. 10, 1974.
- *Size.*—Uniform. Large to medium. Average diameter axially—2⅛". Average transversely in suture plane—2⅛".
- *Form.*—Symmetrical. Globose.
- *Suture.*—Distinct. Shallow. Extends from base to apex.
- *Ventral surface.*—Rounded slightly.
- *Cavity.*—Rounded. Shallow.
- *Base.*—Flat.
- *Apex.*—Short. Depressed.

Skin:
- *Thickness.*—Medium.
- *Tendency to crack.*—None noted.
- *Down.*—Wanting.
- *Color.*—Yellow (10–L–7) substantially entirely overspread with red (7–L–6) shading to darker red (56–L–4). Many yellow flecks.

Flesh:
- *Texture.*—Firm. Fine. Crisp. Meaty.
- *Fibers.*—Few. Tender.
- *Ripens.*—Evenly.
- *Flavor.*—Sub-acid. Delicate.
- *Eating quality.*—Very good to excellent.
- *Color.*—Yellow (12–J–5).

Stone:
- *Type.*—Semifree.
- *Size.*—Medium to small. Average length—⅞". Average breadth—½". Average thickness—⅜".
- *Form.*—Oval.
- *Base.*—Straight.
- *Apex.*—Acute.
- *Sides.*—Equal.

*Tendency to split.*—None noted.

*Color.*—Beige (13–J–7).

Use: Market—local and long distance shipping.

Keeping quality: Very good.

Resistance to insects and diseases: No unusual susceptibilities noted.

Shipping quality: Very good.

The plum tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, which is large, vigorous, upright to spreading, open, foliated with medium size, ovate leaves having a crenate margin, blooming with medium size, white flowers, and a regular and very productive bearer of large to medium, uniform size, symmetrical, globose, semi-freestone fruit, of very good to excellent eating quality, having yellow skin substatially entirely overspread with red, and yellow flesh; the tree, which blooms about with the Santa Rosa and bears late-ripening fruit, being characterized—in comparison to the Casselman—by heavier and more regular production of fruit, the latter having a brighter red color, fewer growth cracks and other fruit defects, and ripening a few days later.

No references cited.

ROBERT E. BAGWILL, Primary Examiner